United States Patent [19]

Pehrson, Sr. et al.

[11] Patent Number: 5,977,087

[45] Date of Patent: Nov. 2, 1999

[54] TOPICAL PREPARATION FOR TREATMENT OF APHTHOUS ULCERS AND OTHER LESIONS

[75] Inventors: David W. Pehrson, Sr., Londonderry; Michael P. Romanowsky, Hampstead, both of N.H.

[73] Assignee: Pehrom Pharmaceutical Corporation, Windham, N.H.

[21] Appl. No.: 07/752,831

[22] Filed: Aug. 30, 1991

Related U.S. Application Data

[63] Continuation-in-part of application No. 07/407,813, Sep. 13, 1989, abandoned.

[51] Int. Cl.$^6$ .................................................. A61K 31/70
[52] U.S. Cl. ........................... 514/53; 536/121; 536/122; 536/124
[58] Field of Search .................................... 536/121, 122, 536/55, 55.1, 125; 514/54, 53; 535/55.1

[56] References Cited

U.S. PATENT DOCUMENTS

| | | | |
|---|---|---|---|
| 4,361,567 | 11/1982 | Bristol et al. | 424/256 |
| 4,668,665 | 5/1987 | Ishihara et al. | 514/53 |
| 4,812,444 | 3/1989 | Mitsulwki et al. | 514/53 |
| 4,945,084 | 7/1990 | Packman | 514/53 |
| 4,990,610 | 2/1991 | Lazaridis et al. | 536/118 |

OTHER PUBLICATIONS

The Merck Index, 9$^{th}$ ed, (1976) No. 1832; 4675, 7360 and 8283; pp. 23, 630, 985 and 1103–1104.

*Primary Examiner*—Elli Peselev
*Attorney, Agent, or Firm*—Hayes, Soloway, Hennessey, Grossman & Hage, P.C.

[57] ABSTRACT

Aphthous ulcers and other lesions of the mucosal, submucosal, epidermal, dermal or subcutaneous tissue of the mouth are treated by a method comprising administering to a patient suffering from such lesion a topical preparation containing sucralfate as an essential ingredient. The invention is also drawn to a preparation comprising sucralfate as an essential ingredient, and a method for preparing the same. The sucralfate is combined with an appropriate pharmaceutical medium to form a homogenous mixture which can then be dispersed in other media to form a preparation useful for topical application to the lesion.

8 Claims, No Drawings

TOPICAL PREPARATION FOR TREATMENT OF APHTHOUS ULCERS AND OTHER LESIONS

This is a continuation-in-part of U.S. application Ser. No. 407,813 filed Sep. 15, 1989, now abandoned.

BACKGROUND

There are several types of lesions of mucosal, submucosal, epidermal, dermal and subcutaneous tissue and various other inflammatory processes for which no effective cure has previously been found. These include aphthous ulcers, lesions of the pharynx, stomatitis, gingivo-stomatitis, cheilosis, and other types of oral lesions or inflammations of the mucosal, submucosal, dermal, epidermal, or subcutaneous tissue. The present invention has particular utility in the treatment of aphthous ulcers and other oral lesions and will be described in connection with such utility, although utility for the treatment of other types of lesions and inflammations is also indicated.

The aphthous ulcer, which is commonly referred to as a canker sore, is a painful oral lesion occuring on the mucous membranes of the tongue, lips, cheek, soft and hard palates, gingiva, floor of the mouth, or pharynx. Several factors have been suggested as possible causes of the disease known as aphthous stomatitis, which is manifested by the formation of aphthous ulcers. However, the disease is still not completely understood, and the factors which cause aphthous stomatitis are still being investigated.

One popular theory is that aphthous stomatitis is caused by stress, whether chemical, physical or emotional. Chemical stress would include consumption of spicy or highly acidic foods which alter the mucosal chemistry. Physical stress would include abrasion or irritation of the mucosal tissue by ill-fitting dentures, orthodontic appliances, or stray toothbrush bristles, as well as other types of physical trauma to the mucosal tissue which may develop into canker sores. Emotional stress resulting from an intense emotional experience, change of environment, or pressures of job, school, or personal relationships have also been associated with the formation of aphthous ulcers.

Hypersensitivity to certain foods has been postulated as a factor which may account for some cases of aphthous ulcers, but there is little evidence to support this suggestion. It is also believed that some aphthous ulcers may be virally induced. The disease has also been linked to hormonal cycles in females, who tend to suffer more frequently from the disease than males. It has been found that women who suffer chronically from the disease are free of lesions during pregnancy. It is also common for cancer patients undergoing chemotherapy to suffer from severe and persistent aphthous ulcers, which may appear in large numbers.

Even though the foregoing and other factors have been suggested as contributory to the disease, aphthous stomatitis is found in children and adults, males and females, patients with or without gastrointestinal problems, and patients with good or poor general health. There is some evidence of patterns in families of patients who are prone to developing aphthous ulcers which suggests that heredity may play a role in whether or not a patient may be susceptible to the disease. Although the foregoing as well as other factors have been examined, no definitive explanation of the mechanism of the formation of aphthous ulcers has been determined.

The ulcers typically last from 5 to 21 days. Often the ulcers form in groups and merge into a singular extensively ulcerated area. The lesions may become extremely painful, especially during periods of fatigue or during eating, which may become difficult if not impossible.

The treatment of aphthous ulcers, and lesions of the mouth in general, has heretofore only involved protecting, anesthetizing, and/or soothing the affected area as needed to ease patient discomfort until healing of the lesion is complete. The most common treatments have included the use of local anesthetics, astringents, antiseptics, protective preparations, and topical steroids. These treatments only serve to treat the problem symptomatically, temporarily relieving or reducing pain, cooling the area of the lesion, protecting the ulcer against further irritation, or reducing inflammation. Another treatment, described in U.S. Pat. No. 4,191,750 uses primarily potassium nitrate in a glycerol base as a topical preparation and reports some success with reduction of pain and promotion of healing. Potassium nitrate is an antiseptic and astringent agent which shows some benefit in the promotion of healing, but its primary benefit as applied to canker sores appears to be as an anesthetic. That preparation appears to have a relatively prolonged desensitizing effect, but it has the disadvantage of causing stinging during application before it takes effect as an anesthetic. There has been no effective method or preparation which provides a cure for aphthous ulcers.

It is therefore an object of the present invention to provide an effective treatment for aphthous ulcers which actually resolves the area of ulceration.

It is a further object of the present invention to provide a new method of preparing an effective topical treatment for aphthous ulcers.

Another object of the present invention is to provide an effective topical treatment for lesions of the mucosal tissue, including tissues of the mouth, tongue, and pharynx.

A still further object of the present invention is to provide an effective topical treatment for lesions resulting from stomatitis, gingivo-stomatitis, or cheilosis.

A still further object of the present invention is to provide an effective topical treatment for various oral lesions of the mucosal, submucosal, dermal, epidermal, and subcutaneous tissues.

Yet another object of the present invention is to provide new methods of preparing topical treatments for various oral lesions of the mucosal, submucosal, dermal, epidermal, and subcutaneous tissues.

Other objects, features and advantages will become apparent from the following description of the invention.

SUMMARY OF THE INVENTION

The present invention relates to a topical preparation which resolves aphthous ulcers and in most cases cures the lesion within 24–48 hours. Modified forms of the preparation are used to effectively treat chemically-induced micro-ulcerations of the pharynx, stomatitis, gingivo-stomatitis, cheilosis, and second-degree burns of the mucosal tissue. The invention is also an effective treatment for other lesions of the mucosal, submucosal, epidermal, dermal, and subcutaneous tissues.

The preparation of the present invention comprises sucralfate as its active ingredient. Sucralfate is a disaccharide polysulfate-aluminum compound, more specifically referred to as α-D-Glucopyranoside, β-D-fructofuranosyl, octakis-(hydrogen sulfate), aluminum complex. The structure of the compound is as follows:

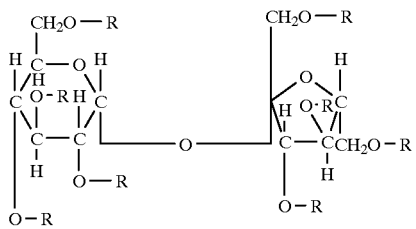

where $R=SO_3[Al_2(OH)_5 (H_2O)_2]$.

U.S. Pat. No. 3,432,489 reports that compounds of this type, described therein as disaccharide polysulfate-aluminum compounds containing 7–13% sulphur and 11–24% aluminum per molecule, display peptic ulcer inhibiting action. Sucralfate has become widely prescribed in tablet form for patients with duodenal ulcers. The drug has shown remarkable effectiveness in these patients as an antiulcer agent which actually accelerates the healing of the ulcer at its site. However, use of sucralfate in a topical application for oral lesions of the mucosal, submucosal, dermal, epidermal, or subcutaneous tissue has heretofore not been suggested.

Until the development of the present invention, sucralfate has not been known to be an effective treatment for aphthous ulcers, nor for similar oral lesions for which topical application of a treatment is indicated. Furthermore, to topically apply sucralfate would not have been considered practical, due to its physical properties which present difficulty in using the drug as such. Sucralfate is insoluble in water, alcohol, most organic solvents and mixed vehicles. It is freely soluble in most concentrated organic acids. Sucralfate cannot be mixed with traditional gums or resins used as emulsifying agents, since they will bind the molecule and render it unavailable for therapeutic effect.

The present invention is drawn to the use of sucralfate as a topical preparation for the treatment of oral lesions of the mucosal, submucosal, epidermal, dermal, or subcutaneous tissue, the pharmaceutical preparation containing sucralfate for such uses, and a method of preparing the same. The terms "oral lesion" and "lesion of the mouth" as used herein are meant to include lesions of the lips and adjacent skin, the tongue, the gums and other internal tissue of the oral cavity, and the pharynx.

It has now been found that sucralfate, in admixture with an appropriate pharmaceutical medium, may be topically applied to aphthous ulcers and other lesions to resolve the ulcer or lesion. Appropriate pharmaceutical media would include any pharmaceutical medium which is capable of admixture with the sucralfate without altering its therapeutic effect, in order to form a preparation which can be administered topically to the lesion to be treated. Some forms of administering the sucralfate may include pastes, ointments, oral rinses, liquids for oral administration, lozenges, medicated bandages, sprays, and any other form which may be suitable for topical application to an oral tissue lesion, as long as the medium does not substantially inhibit the therapeutic effect of the sucralfate.

The results produced by topical application of the sucralfate in a paste-type preparation to an aphthous ulcer are, in most cases, resolution of the ulcer within 24–48 hours, in addition to the immediate relief from pain or discomfort provided by the preparation. Similar results have been obtained for other topical preparations of sucralfate to other types of lesions including, for example, lesions of the tongue or pharynx, which are treated with a liquid preparation which is swished and/or swallowed to coat the lesions.

Topical application of sucralfate according to the invention has also provided relief from gingivo-stomatitis (cold sores), and appears particularly effective when the cold sore blister has broken and advanced to the lesion stage.

Other oral lesions of the mucosal, submucosal, dermal, epidermal, and subcutaneous tissue will respond favorably to topical application of sucralfate in an appropriate carrier. Such lesions include stomatitis (lesion or inflammation of the lip); cheilosis (cracking or peeling around the lips or gums); lesions of the pharynx, including chemically-induced ulcerations or lesions; and second-degree burns of the mouth, tongue or lips.

The mechanism by which sucralfate inhibits aphthous ulcers and other lesions is not fully understood. However, it is likely that the mechanism by which the sucralfate cures such lesions is similar to the mechanism by which sucralfate heals peptic and duodenal ulcers.

A topical preparation in the form of a paste containing sucralfate has been developed particularly for use in treating aphthous ulcers. Sucralfate is mixed with at least one suitable pharmaceutical medium to form a homogenous mixture. In the preferred embodiment, the pharmaceutical medium is a demulcent. The demulcent is believed to serve as a suspending or emulsifying medium for carrying the sucralfate. The demulcent mixture may also comprise agents such as emulsifiers, emollients, adsorbents, and surfactants, depending upon the nature of the demulcent(s) used in order to provide a stable emulsion or suspension. Water, propylene glycol, or other solvents suitable for oral drug use may be added alone or in combination to prepare a paste of suitable consistency. Preservatives, colorings and flavorings are also added in the preferred method of preparation in order to produce a pharmaceutically elegant product which is pleasant to use.

In the preferred embodiment, the paste for the treatment of aphthous ulcers is prepared by mixing sucralfate powder in an aqueous medium comprising a demulcent. In this embodiment, carboxypolymethylene is a main ingredient of the demulcent medium of choice, which further comprises polysorbate 80 as an emulsifying agent. The demulcent medium in the preferred embodiment also contains simethicone to eliminate foaming. Upon trituration of the demulcent medium with the sucralfate, a homogenous mixture is thereby formed, although it is not known whether this mixture is a suspension or an emulsion, or whether there has been a chemical reaction to form a polymer. Once obtained, the sucralfate mixture is then capable of being mixed with a medium comprising another demulcent, preferably a cellulose derivative such as methylcellulose in aqueous solution, to form a paste which has protective and adherent properties but has not rendered the sucralfate inactive in its therapeutic effect. A small amount of the paste is applied directly to the oral lesion, which preferably has been preliminarily dried with gauze or a cotton swab to enhance adhesion of the paste to the lesion.

In another embodiment of the invention, the initial mixture of a demulcent medium and the sucralfate is mixed with a liquid such as lactulose syrup before triturating with the methyl-cellulose solution. The resultant liquid suspension/emulsion is useful for the treatment of multiple oral lesions, which are often suffered by cancer chemotherapy and radiation patients. The liquid is swished in the mouth for as long as possible to maximize contact of the lesions with the drug. The liquid is then expectorated.

Further embodiments of the invention include preparation of a sucralfate/demulcent-medium mixture into a lozenge for treatment of aphthous ulcers, and a liquid to be swished in the mouth and swallowed for the treatment for chemically-induced micro-ulcerations of the pharynx.

EXAMPLE 1

An oral paste for the treatment of aphthous ulcers (canker sores), oral lesions associated with orthodontic appliances, oral. lesions associated with chemotherapy and radiation, and certain other oral lesions or irritations including stomatitis, gingivo-stomatitis and cheilosis was prepared. 5 Carafate tablets (1 g. Sucralfate/tablet, Marion Laboratories) were crushed, and the resultant powder was triturated with Vehicle-S™ (Paddock Laboratories), which is an aqueous mixture of carboxypolymethylene, polysorbate 80 and simethicone, with methylparaben as a preservative. The trituration was performed by geometric progression in a porcelain mortar until a relatively smooth paste was obtained.

The resulting material was a gritty, light-purple paste which was scraped from the sides of the mortar and triturated by geometric dilution with 4 ml. of Cologel™ methylcellulose oral solution (Lilly), which contains methylcellulose, citric acid, FD&C yellow #6, flavor, monosodium glutamate, propylene glycol, saccharin, sodium propionate and water. Trituration was continued until a uniform paste was obtained.

EXAMPLE 2

An oral paste for the treatment of aphthous ulcers and certain other lesions or irritations, as set forth in Example 1, was prepared. 5 grams of sucralfate powder (Paddock Laboratories) was triturated with Vehicle-S™ (Paddock Laboratories), which is an aqueous mixture of carboxypolymethylene, polysorbate 80 and simethicone, with methylparaben as a preservative. The trituration was performed by geometric progression in a porcelain mortar until smooth. Trituration was continued for 5 minutes, and the resultant mixture was covered and allowed to dry overnight.

The resulting material was a smooth, gelatinous material, which was scraped from the sides of the mortar and triturated by geometric dilution with 4 ml. of Cologel™ methylcellulose oral solution (Lilly), which contains methylcellulose, citric acid, FD&C yellow #6, flavor, monosodium glutamate, propylene glycol, saccharin, sodium propionate and water. Trituration was continued until characteristic emulsion cracking was observed. The mixture was allowed to stand for about 15 minutes or until all of the liquid was absorbed, then the mixture was triturated again until smooth.

EXAMPLE 3

An oral paste for the treatment of aphthous ulcers and certain other lesions or irritations, as set forth in Example 1, was prepared. 5 grams of sucralfate powder was triturated with 7 ml. of Vehicle-S™ by geometric dilution in a porcelain mortar until a homogenous smooth past was formed. The resultant mixture was covered with paper and allowed to stand for 24 hours until a smooth, gelatinous material was formed, as in Example 1.

The gelatinous material was then triturated until impalpable, then 4 ml. of Cologel™ and 300 mg. of methylcellulose (4000 C.P.S., U.S.P.) was triturated into the gelatinous material by geometric dilution in the porcelain mortar until characteristic emulsion cracking was observed. Aggressive trituration was continued for 5 minutes beyond the cracking stage. The paste was then packaged in 5 g. collapsible metal tubes and protected from excessive heat and direct sunlight.

The resultant paste is administered for treatment of aphthous ulcers by drying the oral mucosa with gauze or a cotton swab in the area including the lesion. A pea-sized portion of the paste is then applied to the affected area, preferably every 2 hours until the lesion is healed. Eating or drinking should be avoided for a period of time after application. The paste adheres well to oral mucosa when pressed into place. Rubbing the paste will decrease adhesion. The typical healing response occurs usually within 24 hours.

EXAMPLE 4

A paste for the treatment of aphthous ulcers and certain other lesions was prepared as in the method of Example 3, with the further addition of 0.5% hydrocortisone acetate to the mixture before final trituration of the preliminary powder with the Cologel™. The resultant paste is administered for treatment as above.

EXAMPLE 5

An oral rinse for the treatment of multiple aphthous ulcers or other oral lesions was prepared. 10 grams of sucralfate powder was triturated with Vehicle-S™ until smooth in a wedgewood mortar and allowed to dry for 24 hours. 36 ml. of lactulose syrup (Barre Labs) was added by geometric progression with continuous trituration in a glass mortar. When the solution was of a homogenous nature, 5.4 grams of methylcellulose was added by geometric progression with continuous trituration.

The resulting liquid is administered for treatment for oral lesions as follows: 2–4 ml. of liquid is swished on each side of the mouth for as long as possible in order to coat the lesions. The liquid is then expectorated to avoid the possible laxative effect that orally ingested lactulose may cause. This formulation is especially useful in patients suffering from large numbers of lesions, including cancer chemotherapy and radiation patients suffering from multiple aphthous ulcers.

EXAMPLE 6

A lozenge for the treatment of aphthous ulcers was prepared. 5 grams of sucralfate powder was triturated with 10 ml. of Vehicle-S™ as above and allowed to stand for about 4 hours. To this mixture was added 5 grams of Citrocel™ (Lakeside Labs) with continuous trituration until a smooth paste was formed. (Each 19 g. packet of Citrocel™ contains methylcellulose (2 g.), citric acid, FD&C Yellow #6, natural and artificial orange flavor, potassium citrate, riboflavin and sucrose.) The resultant paste was poured into a lozenge mold, with each cavity having a capacity of 1.2 g. The mixture was allowed to air dry for about 5 days, or until the lozenges were hard enough to be removed from the mold.

The resultant lozenge is pleasant tasting and affords prolonged contact time of the sucralfate with the oral lesion, which is desirable for optimum effectiveness in curing the ulcer.

EXAMPLE 7

A liquid for the treatment of lesions of the mouth or pharynx, including chemically-induced pharyngeal injuries, was prepared. 2.7 grams of methylcellulose was added to about 240 cc. of Vehicle-S™ by geometric progression, and the mixture was triturated until smooth. In a separate vessel, 20 grams of sucralfate powder was triturated with about 20 cc. of Vehicle-S™. This mixture was added to the methylcellulose mixture. 30 cc. of strawberry syrup (Sugar Mill Industries) was then added along with a sufficient quantity of Vehicle-S™ to bring the volume of the mixture to 240 cc., or about 8 ounces. (The strawberry syrup contains corn sweetener, water, sugar syrup 85% w/v, natural and artificial flavors, citric acid, less than $\frac{1}{10}$ of 1% sodium benzoate, potassium sorbate and color.)

The resultant liquid was bottled and refrigerated. Before use, the liquid should be shaken well. It is orally administered for the treatment of lesions of the mouth or pharynx in a dose of from 2.5–5.0 cc. which is swished in the mouth and/or then swallowed to coat the pharynx. The dosage should be repeated about every two hours until the lesions are resolved.

EXAMPLE 8

A liquid suspension for the treatment of lesions of the mouth or pharynx, including chemically-induced pharyngeal injuries, was prepared. 12 grams of sucralfate was triturated with 600 mg. hydrocortisone acetate in a wedgewood mortar until impalpable. 30 ml. of Vehicle-S™ was added by geometric progression with continuous trituration until a smooth paste was formed. 90 ml. of Cologel™ was added to this mixture by geometric progression, with continuous trituration until a smooth suspension was formed. The resultant liquid was packaged in a 4 oz. plastic bottle. The suspension should be shaken well before use. It is orally administered for the treatment of lesions of the mouth or pharynx in a dose of 2.5 to 5.0 ml. which is swished in the mouth and/or swallowed to coat the pharynx. The dose should be repeated about every two hours until the lesions are resolved.

EXAMPLE 9

A liquid suspension for the treatment of lesions of the mouth, including lesions of the gums, tongue, and oral mucosa, was prepared. 10 grams of sucralfate was triturated with 1 g. methyl cellulose (4000 C.P.S., U.S.P.). Sufficient Vehicle S was admixed to make 60 ml. of thick, homogenous liquid. The suspension is applied with a dropper to the affected area.

Eight patients suffering from aphthous ulcers were administered the paste preparation of the invention prepared in accordance with Example 1, above. Patients were instructed to apply the paste to the affected area every 2–3 hours during the day and repeated at bedtime. Despite patient reports of difficulty with the texture, taste, and ease of application of this formulation, all patients reported pain relief and significant healing within 72 hours of first application of the paste.

Improved paste formulations were developed, as set forth in Examples 2–4, above, which solved the problems of texture, taste and ease of application which were present in the paste of Example 1.

A study of 25 patients diagnosed with oral lesions was conducted wherein 15 of the patients used the paste prepared in accordance with Example 3, and 10 of the patients used the paste prepared in accordance with Example 4. Each patient in the study had a confirmed diagnosis of aphthous ulcers characterized by abscessed ulcerations, traumatic ulcerations secondary to orthodontia, or micro-ulcerations secondary to cheilosis. The patient population varied in age from 9 years to 55 years, consisting of 16 females and 9 males. The oral lesions measured from 1 ml. to 1 cm. In 50% of the cases, multiple lesions were present.

The patients were instructed to use the preparation once every 2 to 3 hours as necessary for palliation and healing. The paste was administered by drying the affected area with gauze or a cotton swab, then applying a pea-sized amount of the paste with the finger to the lesion.

The 15 patients using the preparation in accordance with Example 3 consisted of 7 males and 8 females. That group reported the following results:

PAIN RELIEF:

9 patients reported relief of pain in one hour or less.

5 patients reported relief of pain in 24 hours or less.

1 patient reported no pain relief.

HEALING:

5 patients reported healing in 24 hours or less.

5 patients reported healing in 48 hours or less.

2 patients reported healing in 72 hours or less.

3 patients reported healing in 120 hours or less.

The 10 patients using the preparation in accordance with Example 4 consisted of 2 males and 8 females. That group reported the following results:

PAIN RELIEF:

4 patients reported relief of pain in one hour or less.

4 patients reported relief of pain in 24 hours or less.

2 patients reported no pain relief.

HEALING:

5 patients reported healing in 48 hours or less.

2 patients reported healing in 72 hours or less.

1 patient reported healing in 96 hours or less.

2 patients reported healing in 120 hours or less.

With respect to differences in efficacy between the formulations of Examples 3 and 4, it appears that the formulation of Example 4, which contains hydrocortisone acetate as an additive, produced no better results in pain relief or healing than the formulation of Example 3, which contains no hydrocortisone. It can therefore be concluded that the presence of sucralfate provides both pain relief and promotion of healing and that its efficacy is not enhanced by the addition of hydrocortisone.

The overall results of the study of the 25 patients showed that 16% of the patients reported that they were free of all oral lesions within 24 hours. 44% of the patients reported that they were free of all oral lesions within 48 hours. Thus, 60% of the patients studied reported complete healing within 48 hours. Another 16% of patients reported complete healing within 72 hours. 24% of the patients reported healing within 4 to 5 days. Thus, a majority (76%) of the patients reported complete healing within the first 3 days of beginning treatment.

With respect to palliation and capacity to resume normal eating and drinking, 72% of the patients reported experiencing palliation within the first hour of treatment following application of the preparation. The patients noted that they were able to return to eating in a normal fashion within one hour as well as being able to tolerate liquids without pain throughout that time period. 86% of the patients reported moderate to marked resolution of symptoms within 24 hours.

96% of the patients had tried more than one other preparation in the past for treatment of oral lesions. The patient group reported that upon suffering previous occurrences of such oral lesions, healing required anywhere from 5 to 10 days with use of other preparations.

100% of the patients experienced no side effects of the preparation used in the study.

In a separate study, two patients suffering from oral lesions at the lower gum line were administered the liquid suspension of Example 9, above. Relief and significant healing in both patients within 72 hours was reported.

It appears that the sucralfate powder is most successfully combined with a demulcent, in particular carboxypolymethylene, when an emulsifying agent is also present. The emulsifying agent in the Vehicle-S™ used in the examples is polysorbate-80. In addition, an adsorbant such as simethicone, which is also an ingredient of Vehicle-S™, is useful to alleviate the foaming which occurs during the admixing of the sucralfate with the demulcent. This preliminary mixture of the sucralfate and demulcent is triturated into a frosting-like form and dried to a smooth, gelatinous material. That suspension/emulsification process involves a reaction of unknown mechanism. The resulting gelatinous material is easily suspended or emulsified, utilizing common pharmaceutical hydrocolloids, anionic surfactants, lactulose and a variety of other official vehicles, to produce a stable formulation. It is suspected that the preliminary gelatinous material is capable of forming a stable mixture in a wide variety of aqueous media and demulcents suitable for oral or topical use on mucosal, submucosal, epidermal, dermal, and subcutaneous tissue. It is theorized that polyethylene compounds, polyvinyl alcohols, and a wide variety of demulcents would work equally well as a vehicle for the preliminary powder material. It is known that natural gums and resins, such as tragacanth, acacia, and kaolin, will bind the sucralfate and render it inactive.

Several additives have been contemplated for use in the sucralfate treatments for mucosal tissue and skin, as well as for submucosal, dermal, epidermal and subcutaneous tissues. Such additives include analgesics such as aspirin, codeine, ibuprofen, and tincture of opium; topical anesthetics such as Cetacaine (Cetylite Industries) and lidocaine hydrochloride, marketed as Xylocaine (Astra Pharmaceuticals); antibiotics such as penicillin, garomycin, tetracycline, and cephalosporin-type antibiotics; antifungals such as Polymyxin™ (Burroughs Welcome); antihistamines such as Benadryl™; steroids such as hydrocortisone, triamcinolone and fluocinolone; minerals such as magnesium, calcium, selenium, zinc, and phosphorus; and other miscellaneous additives including prostaglandins, topical epinephrine, and oxytocin. Many of these additives are particularly desirable for use in the paste preparation for the treatment of aphthous ulcers and other oral lesions.

There are, of course, countless alternative pharmaceutical media in which the sucralfate may be carried. In addition, other methods of administering the sucralfate to the lesion will occur to one skilled in the art. For example, a lollipop containing a therapeutically effective amount of sucralfate may be a desirable method of administration of the drug, particularly to children suffering from aphthous ulcers.

It is believed that a wide variety of lesions of the mucosal, submucosal, epidermal, dermal, and subcutaneous tissues, including second-degree burns, may be effectively treated by topical application of sucralfate.

Other topical uses and formulations of sucralfate for treatment of lesions of the mucosal, submucosal, epidermal, dermal, and subcutaneous tissues may occur to one skilled in the art without departing from the spirit and scope of the invention.

We claim:

1. A method of treating a patient suffering from an aphthous ulcer, the method comprising administering to said patient a topical preparation containing sucralfate as an essential ingredient, wherein:

(a) the sucralfate is admixed with an aqueous carboxypolymethylene medium containing polysorbate 80 and simethicone, said medium being added to said sucralfate in an amount sufficient to form a paste;

(b) the mixture is allowed to dry; and (c) the resulting material is dispersed in an aqueous methylcellulose medium;

and wherein said preparation is topically applied to said aphthous ulcer in an amount sufficient to cover said aphthous ulcer.

2. A process of preparing a pharmaceutical preparation for treatment of an aphthous ulcer, the process comprising:

(a) triturating sucralfate powder with an aqueous mixture of carboxypolymethylene, polysorbate-80 and simethicone to form a substantially homogenous mixture, said aqueous mixture being added to said sucralfate in an amount sufficient to form a paste;

(b) allowing said substantially homogenous mixture to dry into a gelatinous material; and (c) mixing said gelatinous material with an aqueous methylcellulose medium to form a preparation for topical application to said aphthous ulcer.

3. The method of claim 1, wherein said topical preparation also contains hydrocortisone acetate.

4. The method of claim 1, wherein said sucralfate in admixture with said aqueous carboxypolymethylene medium is mixed with lactulose before dispersion in said aqueous methylcellulose medium.

5. The method of claim 1, wherein said topical preparation is formed into a member of the group consisting of an oral paste, an oral rinse, a lozenge, an ointment, a spray, and a liquid to be swallowed.

6. The process of claim 2, wherein said preparation also contains hydrocortisone acetate.

7. The process of claim 2, wherein said substantially homogenous mixture is mixed with lactulose before dispersing said mixture in said aqueous methylcellulose medium.

8. The process of claim 2, wherein said preparation is formed into a member of the group consisting of an oral paste, an oral rinse, a lozenge, an ointment, a spray, and a liquid to be swallowed.

* * * * *